US00PP15464P3

(12) United States Plant Patent
Redman

(10) Patent No.: US PP15,464 P3
(45) Date of Patent: Jan. 4, 2005

(54) ***CHRYSANTHEMUM* PLANT NAMED 'VULCAN TIME BRONZE'**

(50) Latin Name: *Chrysanthemum morifolium*
Varietal Denomination: Vulcan Time Bronze

(75) Inventor: Ruth Redman, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 0 days.

(21) Appl. No.: 10/365,162

(22) Filed: Feb. 11, 2003

(65) Prior Publication Data

US 2004/0158899 P1 Aug. 12, 2004

(51) Int. Cl.[7] ..... A01H 5/00
(52) U.S. Cl. ..... Plt./286
(58) Field of Search ..... Plt./286, 296

(56) References Cited

PUBLICATIONS

Brummitt, 1997. The Garden, Horticultural Science: Chrysanthemum once again, pp. 662–663.*
2002 CBA (Chrysanthemum Breeders Association) catalogue excerpt listing the variety "Virunga Bronze." (Best copy available, no photograph).
2003 CBA (Chrysanthemum Breeders Association) catalogue listing the variety "Virunga Bronze." See, e.g., pp. 17 and 18 (color photograph).
U.S. Plant patent application Publication No. US 2003/0009809 P1, pub. date Jan. 9, 2003, Appl. No. 09/900,234 filed Jul. 6, 2001, for variety 'Vulcan Time,' inventor Mark Roland Boeder.
1998 Ficor catalog listing variety 'Vulcan Time.' See, e.g., p. 4.
1999 Ficor catalog listing variety 'Vulcan Time.' See, e.g., p. 4.
2000 Ficor catalog listing variety 'Vulcan Time.' See, e.g., p. 4.
2001 Ficor catalog listing variety 'Vulcan Time.' See, e.g., p. 4.
2002 Ficor catalog listing variety 'Vulcan Time.' See, e.g., p. 4.
* cited by examiner

*Primary Examiner*—Anne Marie Grunberg
*Assistant Examiner*—June Hwu
(74) *Attorney, Agent, or Firm*—Howrey Simon Arnold & White LLP

(57) ABSTRACT

A new variety of *Chrysanthemum* plant named 'Vulcan Time Bronze,' having a good uniform canopy of bronze single flowers expressing a central longitudinal yellow striping and a yellow base around a light green disc. The new variety has a medium tall vigor, free branching, uniform spreading habit and good foliage presentation.

1 Drawing Sheet

Latin name of the genus and species: Botanical classification: *Chrysanthemum morifolium.*

Variety denomination: The new *Chrysanthemum* variety denomination is 'Vulcan Time Bronze.'

BACKGROUND OF THE INVENTION

The present invention comprises a new and distinct cultivar of *Chrysanthemum* botanically known as *Chrysanthemum morifolium,* and referred to by the cultivar name 'Vulcan Time Bronze.'

'Vulcan Time Bronze,' identified as 20247-2, originated from a naturally occurring whole plant mutation grown in a controlled planting of the variety 'Vulcan Time' (U.S. Plant patent application Publication No. US 2003/0009809), in Chichester, West Sussex, United Kingdom. The new variety 'Vulcan Time Bronze' has been asexually reproduced by vegetative cuttings in Chichester, West Sussex, United Kingdom and the distinguishing characteristics are retained through successive generations of asexual reproduction.

BRIEF SUMMARY OF THE INVENTION

'Vulcan Time Bronze' is a pot type of *Chrysanthemum* plant variety having bronze single flowers expressing a central longitudinal yellow striping and a yellow base around a light disc.

Comparison with Parent

Plants of the new *Chrysanthemum* variety 'Vulcan Time Bronze' are similar to the parent 'Vulcan Time' in plant habitat and growth rate. In side-by-side comparisons in Chichester, West Sussex, United Kingdom, under commercial practice, plants of the new *Chrysanthemum* variety 'Vulcan Time Bronze' differed from the plants of the parent 'Vulcan Time' in the following characteristics.

1. The new variety 'Vulcan Time Bronze' produces bronze single flowers whereas the parent 'Vulcan Time' produces red single flowers.
2. Plants of the new variety 'Vulcan Time Bronze' have similar inflorescence to the plants of the parent 'Vulcan Time.'

Comparison with Other Varieties

Plants of the new *Chrysanthemum* variety 'Vulcan Time Bronze' are similar to the unpatented 'Virunga Bronze' in plant habit and growth rate. However in side-by-side comparisons in Chichester, West Sussex, United Kingdom, under commercial practice, plants of the new *Chrysanthemum* variety 'Vulcan Time Bronze' differed from plants of 'Virunga Bronze' in the following characteristics.

1. The new variety 'Vulcan Time Bronze' produces dark bronze single flowers whereas 'Virunga Bronze' produces bronze flowers.

2. Plants of the new variety 'Vulcan Time Bronze' have larger and taller inflorescence than plants of 'Virunga Bronze.'

BRIEF DESCRIPTION OF ILLUSTRATION

Typical specimens of the plant and flowers for the new *Chrysanthemum* variety 'Vulcan Time Bronze' are shown in the accompanying digital photograph. The colors shown are as true as possible within the usual limits of this kind of illustration.

FIG. 1 is a whole plant view of the new variety 'Vulcan Time Bronze' grown in a pot. The plant shown in the illustration is 60 days from the commencement of Short Days.

DETAILED BOTANICAL DESCRIPTION

The following description of the new *Chrysanthemum* variety 'Vulcan Time Bronze' is of plants grown in a greenhouse in Chichester, West Sussex, United Kingdom in the month of May. The cultivar has not been observed under all possible environmental conditions. The phenotype may vary significantly with variations in the environment such as temperature, length of day and light intensity, without any variance in genotype. The commercial classification of the new variety is a pot *Chrysanthemum*.

Plants of the new variety have been grown successfully under temperature conditions averaging about 19° C. at night and about 17° C. to 24° C. during the day under light conditions of about 5000 to 6000 foot candles. The plants respond well to the use of growth retardant, such as B9 treatment at about 2 g per liter. To produce a commercial product the plants may be pinched once with the center bud removed. The typical container size for commercial growth is 1 liter. It has been observed that the shelf life of the new variety is about 21 days with a response time of about 8 weeks. The new variety is suitable for growth in a temperature range of 15° C. to 25° C.

The new variety may be produced as a spray. The following description is with respect to a plant produced as a pot *Chrysanthemum*. In the description of this new *Chrysanthemum* variety, color values have been taken The Royal Horticultural Society Colour Chart (R.H.S.C.C.).

Plant

Plant type: Pot.
Habit: Upright.
Height: 28 cm.
Width: 32 cm.
Branching characteristics: Upright and free branching.
Length of lateral branches: 17 cm.
Diameter of lateral branches: 0.5 cm.
Texture of lateral branches: Slightly pubescent.
Number of breaks from pinch: 5.
Stem color: 137B.
Response time: 56 days.
Vigor: Medium/tall.
Shelf life: 21 days.
Disease/pest (susceptibility/resistance observed): None observed to date.
Growth retardant type and treatment: 3 applications of 2.5 gm/liter B9 @2, 21 and 28 days after sticking unrooted cuttings.

The plants were grown for 2 weeks in Long Day conditions (20 hours of light) and then transferred to Short Day conditions (13 hours of dark).

Propagation:
*Type.*—Vegetative propagation via stem cuttings.
*Time to rooting.*—14 days with soil temperatures of 18° C.
*Rooting habit.*—After 7 Long Days the first roots emerge and form root primordia. In 14 Long Days a complete root system is developed.

Foliage

Number of leaves per lateral branch: 12.
Compound or single: Single.
Arrangement of leaves: Alternate.
*Shape of leaf.*—Typically 5 lobed ovate.
*Size of leaf.*—Width (cm): 4 Length (cm): 6.
*Leaf apex.*—Acute.
*Base.*—Obtuse.
*Attachment.*—Petioled.
*Aspect.*—Slight undulating.
*Margin.*—Palmately lobed.
*Surface characteristics.*—Top: slightly pubescent. Bottom: Pubescent.
Petiole:
*Color.*—137B.
*Length.*—2.5 cm.
*Diameter.*—0.2 cm.
*Texture.*—Slightly pubescent.
Venation: Net prominent mid-vein at underside.
*Color.*—Upper side: near 144B. Under side: near 144B.
Color:
*Mature leaf, upper side.*—Near 137B; under side: near 138A.
*Young leaf, upper side.*—Near 137A; under side: near 137C.

Flower

Flower appearance: Matte.
Flower type: Single.
Flower form: Slightly cupped.
Flower shape: Round.
Flowering habit: Domed capitulum.
Number of blossoms per branch: 5.
Inflorescence form: Cyme.
*Depth of fully expanded blossoms.*—2 cm.
*Diameter of fully expanded blossoms.*—7 cm.
Phyllaries:
*Number.*—20.
*Color.*—Near 137B.
*Length.*—0.7 to 1.2 cm.
*Width.*—0.1 to 0.3 cm.
*Texture/appearance.*—Pubescent.
Peduncle: Peduncle length is shortest at the terminal flower and progressively longer moving down the stem.
*Length.*—12 cm (average).
*Diameter.*—0.5 cm.
*Color.*—Near 137B.
*Surface.*—Pubescent.
*Habit.*—Slightly curving.
*Strength.*—Moderately strong.
Pedicel:
*Length.*—Terminal: 3 cm; lateral: 4.5 cm.
*Color.*—Near 137B.
*Diameter.*—0.3 cm.

*Surface.*—Pubescent.
*Habit.*—Slightly curving.
*Strength.*—Moderately strong.

Ray florets:
*Form/shape.*—Straight and spatulate with oblong shape.
*Texture/appearance.*—Matte.
*Number per flower.*—30.
*Length.*—3.5 cm; Width: 1 cm.
*Apex.*—Rounded.
*Base.*—Tapered.
*Margin.*—Entire.

Disc florets:
*Form/shape.*—Cylindric.
*Texture/appearance.*—Shiny.
*Number per flower.*—150.
*Length.*—0.6 cm; Width: 0.1 cm.
*Diameter of disc.*—1.3 cm.

Fragrance: None.

Flower bud:
*Length.*—0.8 cm.
*Diameter.*—1.1 cm.
*Form/shape.*—Globular.

General flower color:
1. *Ray florets, upper side.*—Immature: near 41B expressing a central longitudinal striping 24C. Mature: near 41B expressing a central longitudinal striping 24C and base 24C. Older/Fading: near 40D expressing a central longitudinal striping 24D and base 24D.
2. *Ray florets, under side.*—Immature: near 26C. Mature: near 26C. Older/Fading: near 24C.
3. *Disc florets.*—Immature: near 151B. Mature: near 6A. Older/Fading: near 6A.
4. *Bud.*—22B.

Flower progression with age: Flower form does not change but there is slight color change with age.

Lastingness of blooms: About 21 days.

Reproductive Organs

Gynoecium: Present on ray and disc florets.

Ray florets per individual flower:
*Pistil number.*—30.
*Stigma color.*—Near 6C.
*Stigma shape.*—Forked.
*Style color.*—Near 6C.
*Style length.*—0.3 cm.

Disc florets per individual flower:
*Pistil number.*—120.
*Stigma color.*—Near 6C.
*Stigma shape.*—Forked.
*Style color.*—Near 6C.
*Style length.*—0.3 cm.

Androecium: Not observed.

Fruit and seeds: None observed.

What is claimed is:

1. A new and distinct variety of *Chrysanthemum* plant, substantially as described and illustrated herein.

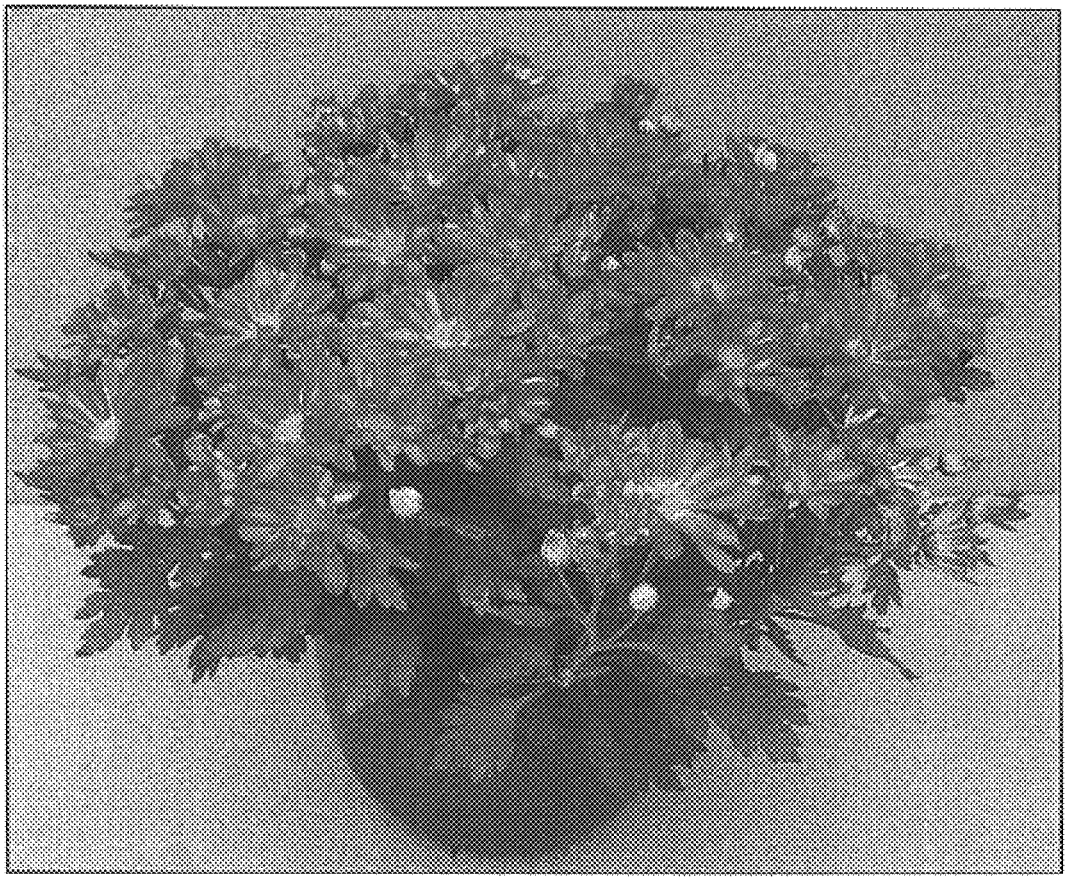

* * * * *